US012765805B2

(12) United States Patent
Arslan et al.

(10) Patent No.: US 12,765,805 B2
(45) Date of Patent: Oct. 20, 2026

(54) SYSTEM FOR FALL DETECTION, FALL PREDICTION, MOBILITY, PHYSICAL AND COGNITIVE FUNCTION ANALYSIS

(71) Applicants: Baturalp Arslan, Lexington, MA (US); Nuri Denizcan Vanli, Boston, MA (US); Murat Bayboga, Izmir (TR); Bulent Yilmaz, Silver Spring, MD (US); Bradley Manor, Amherst, NH (US)

(72) Inventors: Baturalp Arslan, Lexington, MA (US); Nuri Denizcan Vanli, Boston, MA (US); Murat Bayboga, Izmir (TR); Bulent Yilmaz, Silver Spring, MD (US); Bradley Manor, Amherst, NH (US)

(73) Assignee: In The Pendant, Inc., Lexington, MA (US)

( * ) Notice: Subject to any disclaimer, the term of this patent is extended or adjusted under 35 U.S.C. 154(b) by 427 days.

(21) Appl. No.: 18/507,479

(22) Filed: Nov. 13, 2023

(65) Prior Publication Data

US 2025/0152043 A1 May 15, 2025

Related U.S. Application Data

(60) Provisional application No. 63/383,515, filed on Nov. 14, 2022.

(51) Int. Cl.
*G16H 40/67* (2018.01)
*A61B 5/00* (2006.01)
(Continued)

(52) U.S. Cl.
CPC ............ *A61B 5/1117* (2013.01); *A61B 5/002* (2013.01); *A61B 5/0022* (2013.01); *A61B 5/112* (2013.01);
(Continued)

(58) Field of Classification Search
CPC .. A16B 5/02; A16B 5/22; A16B 5/112; A16B 5/486; A16B 5/749; A16B 5/747; A16B 5/681; A16B 5/1117; A16B 5/7275; A16B 5/7267; A16B 5/4842; A16B 5/7282; A16B 5/4884
See application file for complete search history.

(56) References Cited

U.S. PATENT DOCUMENTS 9,011,352 B2 * 4/2015 Ten Kate ........... G08B 21/0446 600/595
9,041,810 B2 * 5/2015 Ecker ..................... G06V 40/25 348/152
2018/0333083 A1 * 11/2018 Orellano ................ G16H 50/30

* cited by examiner

*Primary Examiner* — Nasser M Goodarzi

(57) ABSTRACT

Various embodiments of a system for fall detection, fall prediction, mobility, physical and cognitive function analysis are disclosed. System for fall detection, fall prediction, mobility, physical and cognitive function analysis can receive user data from wearable devices or other sensors and monitors by passive monitoring of the user during normal daily activities and active monitoring of the user during clinically relevant tests. The system can detect falls and alert caregivers in the event of a fall, predict falls and alert user in case there is an imminent fall; analyze, monitor and detect decline in user mobility, physical function and cognitive function, provide relevant feedback to the user or care provider that can be used as targeted information on how to assess, improve, recover or reduce the rate of functional decline.

12 Claims, 9 Drawing Sheets

200

(51) Int. Cl.
*A61B 5/11* (2006.01)
*A61B 10/00* (2006.01)

(52) U.S. Cl.
CPC ............ *A61B 5/4842* (2013.01); *A61B 5/486* (2013.01); *A61B 5/4884* (2013.01); *A61B 5/681* (2013.01); *A61B 5/7267* (2013.01); *A61B 5/7275* (2013.01); *A61B 5/7282* (2013.01); *A61B 5/747* (2013.01); *A61B 5/749* (2013.01); *G16H 40/67* (2018.01); *A61B 2010/0003* (2013.01); *A61B 2503/08* (2013.01); *A61B 2505/07* (2013.01); *A61B 2560/0209* (2013.01)

Sit-to-Stand Analysis Module 400

Turn Analysis Module 500

Fall Risk, Mobility, Physical Function and Cognitive Function Analysis Module 700

Fall Prediction Module 900

SYSTEM FOR FALL DETECTION, FALL PREDICTION, MOBILITY, PHYSICAL AND COGNITIVE FUNCTION ANALYSIS

GOVERNMENT SUPPORT

This invention was made with Government support under Grant Number 2013985 awarded by the National Science Foundation. The Government has certain rights in this invention.

REFERENCES

[1] U.S. Pat. No. 9,011,352B2, "Fall Detection and/or Prevention Systems", Assignee: Koninklijke Philips N V
[2] U.S. Pat. No. 9,041,810B2, "System and Method for Predicting Patient Falls", Assignee: CareView Communications Inc.
[3] L. A. Lipsitz, A. E. Tchalla, I. Iloputaife, M. Gagnon, K. Dole, Z. Z. Su and L. Klickstein, "Evaluation of an Automated Falls Detection Device in Nursing Home Residents", *Journal of the American Geriatrics Society*, vol. 64, no. 2, pp. 365-368, 2016.
[4] L. J. Phillips, C. B. DeRoche, M. Rantz, G. L. Alexander, M. Skubic, L. Despins, C. Abbott, B. H. Harris, C. Galambos and R. J. Koopman, "Using Embedded Sensors in Independent Living to Predict Gait Changes and Falls", *Western Journal of Nursing Research*, vol. 39, no. 1, pp. 78-94, 2017.
[5] B. Manor, W. Yu, H. Zhu, R. Harrison, O-Y. Lo, L. Lipsitz, T. Travison, A. Pascual-Leone, and J. Zhou, "Smartphone App-Based Assessment of Gait During Normal and Dual Task Walking: Demonstration of Validity and Reliability", JMIR mHealth and uHealth, vol. 6, no. 1, 2018.
[6] Shirley Ryan AbilityLab (https://www.sralab.org/)
[7] "STEADI Algorithm for Fall Risk Screening, Assessment and Intervention", Centers for Disease Control and Prevention (CDC), 2019 (www.cdc.gov/steadi)
[8] N. D. Vanli and S. S. Kozat, "A comprehensive approach to universal piecewise nonlinear regression based on trees", *IEEE Transactions on Signal Processing*, vol. 62, no. 20, pp. 5471-5486, 2014.
[9] N. Shazeer, A. Mirhoseini, K. Maziarz, A. Davis, Q. Le, G. Hinton and J. Dean, "Outrageously large neural networks: the sparsely-gated mixture-of-experts layer", *arXiv preprint arXiv:*1701.06538, 2017.
[10] B. Michael and M. Howard. Activity recognition with wearable sensors on loose clothing. PLOS ONE 12(10): e0184642, 2017.
[11] X. Chai et al, "Smart wearables with sensor fusion for fall detection in firefighting", Sensors 21, no. 20, 2021.
[12] L. A. Lipsitz, A. E. Tchalla, I. Iloputaife, M. Gagnon, K. Dole, Z. Z. Su and L. Klickstein, "Evaluation of an Automated Falls Detection Device in Nursing Home Residents", *Journal of the American Geriatrics Society*, vol. 64, no. 2, pp. 365-368, 2016.
[13] J. M. Hausdorff, "Gait dynamics, fractals and falls: Finding meaning in the stride-to-stride fluctuations of human walking," *Human Movement Science*, vol. 26, no. 4, pp. 555-589, 2007.
[14] S. Tanaka, K. Kamiya, N. Hamazaki, R. Matsuzawa, K. Nozaki, T. Nakamura, M. Yamashita, E. Maekawa, C. Noda, M. Yamaoka-Tojo, A. Matsunaga, T. Masuda, and J. Ako, "Short-Term Change in Gait Speed and Clinical Outcomes in Older Patients With Acute Heart Failure", *Circulation Journal*, vol. 83, no. 9, pp. 1860-1867, 2019.
[15] Montero-Odasso M, Verghese J, Beauchet O, Hausdorff J M. Gait and cognition: a complementary approach to understanding brain function and the risk of falling. Journal of the American Geriatrics Society. 2012; 60(11): 2127-36.
[16] O-Y. Lo, M. A. Halko, J. Zhou, R. Harrison, L. A. Lipsitz and B. Manor, "Gait Speed and Gait Variability Are Associated with Different Functional Brain Networks," Front Aging Neurosci, vol. 9, no. 390, pp. 1-8, 2017.
[17] R. A. Sperling, P. S. Aisen, L. A. Beckett, D. A. Bennett, S. Craft, A. M. Fagan, T. Iwatsubo, C. R. Jack Jr., J. Kaye, T. J. Montine, D. C. Park, E. M. Reiman, C. C. Rowe, E. Siemers, Y. Stern, K. Yaffe, M. C. Carrillo, B. Thies, M. Morrison-Bogorad, M. V. Wagster and C. H. Phelps, "Toward defining the preclinical stages of Alzheimer's disease: recommendations from the National Institute on Aging-Alzheimer's Association workgroups on diagnostic guidelines for Alzheimer's disease," *Alzheimers Dement*, vol. 7, no. 3, pp. 280-292, 2011.
[18] M. W. Albers, G. C. Gilmore, J. Kaye, C. Murphy, A. Wingfield, D. A. Bennett, A. L. Boxer, A. S. Buchman, K. J. Cruickshanks, D. P. Devanand, C. J. Duffy, C. M. Gall, G. A. Gates, A-C. Granholm, T. Hensch, R. Holtzer, B. T. Hyman, F. R. Lin, A. C. McKee, J. C. Morris, R. C. Petersen, L. S. Silbert, R. G. Struble, J. Q. Trojanowski, J. Verghese, D. A. Wilson, S. Xu, and L. I. Zhang, "*At the interface of sensory and motor dysfunctions and Alzheimer's Disease*", Alzheimer's and Dementia, vol. 11, no. 1, pp. 70-98, 2015.
[19] M. Montero-Odasso, S. W. Muir and M. Speechley, "Dual Task Complexity Affects Gait in People with Mild Cognitive Impairment: The Interplay Between Gait Variability, Dual Tasking and Risk of Falls", *American Congress of Rehabilitation Medicine*, vol. 93, pp. 293-299, 2012.
[20] M. Di Maio and F. Perrone, "Quality of Life in elderly patients with cancer", *Health Qual Life Outcomes*, vol. 1:44, 2003.
[21] G. H. Guyatt, D. H. Feeny, D. L. Patrick, "Measuring health-related quality of life", *Annals of Internal Medicine*, vol. 118, no. 2, pp. 622-629, 1993.
[22] Lemke N C, Wiloth S, Werner C, Hauer K. Validity, test-retest reliability, sensitivity to change and feasibility of motor-cognitive dual task assessments in patients with dementia. Archives of gerontology and geriatrics. 2017; 70:169-79.
[23] Podsiadlo D, Richardson S. The timed "Up & Go": a test of basic functional mobility for frail elderly persons. Journal of the American Geriatrics Society. 1991; 39(2): 142-8.
[24] Jones C J, Rikli R E, Beam W C. A 30-s chair-stand test as a measure of lower body strength in community-residing older adults. Research quarterly for exercise and sport. 1999; 70(2):113-9.
[25] Tchalla A E, Dufour A B, Travison T G, Habtemariam D, Iloputaife I, Manor B, et al. Patterns, predictors, and outcomes of falls trajectories in older adults: the MOBILIZE Boston Study with 5 years of follow-up. PloS one. 2014; 9(9):e106363.

BACKGROUND

Health, activity and fitness interests of consumers have been increasing immensely. This increase is caused mostly by an increased understanding of the connection between physical activity and wellbeing. Assessing user performance on clinically relevant tests such as timed-up-and-go and 30 seconds sit-to-stand tests in addition to tracking daily activities is important to get clinically meaningful data on user wellbeing. Also, by assessing user performance on tests such as gait speed, 30-seconds sit-to-stand test, dual-task walking test or timed-up-and-go it is possible analyze user mobility, physical function, executive function and cognitive function.

Falls may also have a significant impact on a person's health and wellbeing. Therefore, fall risk assessment, predicting falls, and analyzing possible reasons of falls in order to provide relevant feedback that can possibly reduce fall risk or prevent falls can be very important to maintain function and independence.

Management of dementia and neurodegenerative diseases are also most effective when detected early in the disease state. Gait parameters may serve to identify deficits in executive and/or cognitive function which may serve as a surrogate to identify early dementia states and neurodegenerative diseases, and to track disease progression.

SUMMARY

Present disclosure is directed to a system intended for fall risk assessment, fall detection, fall prediction, active monitoring of user performance on clinically meaningful assessments such as sit-to-stand test (STS) or timed-up-and-go test (TUG), passive monitoring and recording metrics related to user mobility, physical function, cognitive function, executive function, health, and user functional health status, etc.

This invention overcomes limitations in existing work, intending to provide early detection of mobility and cognitive decline that could lead to life altering traumatic falls, or dementia and neurodegenerative diseases. It provides a comprehensive and unified hardware/software platform for: (1) Fall Detection: Machine Learning based fall detection algorithms that are i.) power efficient to run on mobile devices, and ii.) maintain high accuracy since detection metrics are personalized to the user; (2) Fall prevention: Underlying root cause of a recurring fall could be due to mobility, physical (acute or chronic), cognitive, or deficits in the executive functioning of an individual, and identifying these parameters individually is important towards quantifying metrics for fall risk and fall prevention; (3) Ability to provide Dual-task gait assessments, remotely: Gait data collection with respect to dual-task assessments (such as counting back by 3's while normal walking) is critical in assessing a person's executive function, used in identifying mobility and cognitive health; (4) Data collection from habitual setting: Data collection from a clinical setting relies on sophisticated/expensive clinical resource (staff, equipment, etc.) setup and/or monitoring setup that captures motion signatures using a camera/video system. In the clinical setup case, it requires subjects to perform gait tests at a clinician's office, where subjects are typically in their best form limiting the performance value of such gait assessments whereas the ability to perform and collect these metrics within the users' habitual setting provides a more accurate metric of functional performance, compared to data collection from a clinician office; (5) Context-aware information: A person could show acute mobility decline due to a recent medication, temporary dehydration, or depression, not that they are particularly at risk for a fall; (6) combining metrics in a hardware/software platform to evaluate the concept of functional health, which includes mobility or physical function, cognitive function, and executive function. (7) Fall Risk Assessment: Algorithms that quantify clinically-meaningful gait metrics based on their mobility gait assessment, cognitive gait assessment, and physical function gait assessment, taking into account their current health status, to provide a fall risk score categorizing people into low risk (green band), medium risk (yellow band) and high risk (red band) for a potentially life-altering type traumatic fall, and providing metrics for areas to specifically improve and minimize fall risk. This could also provide an objective measure for the need to be in care; (8) "Quality of Life" Assessment: to provide an objective metric to assess the quality of life of a patient (such as geriatric cancer patients) for physical reserve in the determination of treatment options, and to track physical function during and after treatment.

Further, the invention includes a mobile application using either InThePendant's wearable or a commercially available wearable, such as an Apple Watch, that provides a prescribed, in a very specific manner, set of voice-guided physical movements that capture daily variations in dual task-gait and physical function that can be used for detecting the pre-clinical and prodromal stages of amnestic and non-amnestic Mild Cognitive Impairment (aMCI, naMCI) and Alzheimer's Disease and Related Dementias (ADRD). The assessment provides the ability for high-frequency monitoring of proven laboratory-based assessments, conducted remotely, from the user's habitual setting. The Application enables completion of evidenced-based tests and monitoring of clinically-meaningful outcomes on a regular basis. Such high-frequency monitoring enables tracking of daily variation in performance, which is more sensitive to initial pathology than a 'snapshot' of performance in time (e.g., annual clinical visit), or even one's mean performance over time. When used over extended periods, high-frequency monitoring further affords estimation of when an individual's performance deviates from 'normal' in a meaningful way. This approach is critical to the development of 'digital biomarkers' of functional health for people living with ADRD.

Specifically, this system for fall detection, fall prediction, mobility, physical and cognitive function analysis includes one or more wearable devices that may have one or more motion sensors such as but not limited to accelerometers and gyroscopes for detecting motion of the device and providing data of the detected motions. In some embodiments, wearable device may also include one or more feedback devices such as but not limited to speakers, used to provide notice or feedback to the user. Wearable device also may include one or more input devices such as but not limited to buttons or microphones. Wearable device also may include one or more processors for monitoring motion, for processing one or more metrics of the user, for determining when a user falls. In some implementations, wearable device may further include a memory to store sensor data. Processors may be configured to store and retrieve motion data from memory. In some implementations, wearable device may be worn as a freely moving pendant or can be attached to a user's body, such as, trunk, extremities or head. In some implementations wearable device may include other sensors such as but not limited to barometer, temperature/humidity sensor. Wearable device may also include a network interface. Wearable device may also have wake word detection.

In this patent disclosure, some implementations of the system for fall detection, fall prediction, mobility, physical and cognitive function analysis may include: one or more wearable devices with previously disclosed sensors and features, a server (which may be a local server, implemented in a cloud, or in any other method) and associated mobile app all of which are connected through a network. A mobile application or "mobile app" is a computer program or software application designed to run on a mobile device such as a phone, tablet, or watch (hereinafter referred to as mobile app). Some implementations may also include other wearable or non-wearable devices such as heart-rate sensors, blood pressure sensors, and other monitors etc. Wearable device network interface may be configured to transfer data between wearable device, server and associated mobile app.

In some implementations, the server in the disclosed system may be configured to collect output data from one or more previously disclosed wearable devices, process the wearable device outputs that may include scores on user performance related to user mobility, cognitive function, fall risk, fall detection algorithms that may include but are not limited to machine learning based fall detections, fall prediction algorithms that may include but are not limited to machine learning based fall predictions, generate feedback on user performance and transmit them to associated mobile app.

In some implementations of the disclosed system based on gait and movement analysis for clinical or in-home remote fall risk assessment, mobility assessment, physical and cognitive function assessment, fall detection and fall prediction are disclosed. The disclosed system may include various software modules for classifying movements and processing raw data from gait or other body movements such as sitting down, standing up and turns to generate metrics for fall risk assessment, mobility assessment, physical function assessment, cognitive function assessment, for machine learning based fall detection or fall prediction such as but not limited to gait analysis module, sit-to-stand analysis module, fall prediction module, fall detection module, etc.

In some implementations, disclosed system can be used for both active monitoring, where the user performs a prescribed clinically relevant test routines which may include tests like normal walk, dual-task walk, fast walk, 30 second sit-to-stand-test, timed-up and go, balance test or for passive monitoring, where the system collects metrics as the subject performs normal activities of daily living in order to collect user data for fall risk, mobility, physical or cognitive function assessment.

In some implementations, some of the user feedback generated by the disclosed system may be generated by wearable device or the server can be specifically designed to be actionable so the user can use the feedback to reduce fall risk and prevent future falls and can be transmitted to associated mobile app through the network.

In some implementations, disclosed system for fall detection, fall prediction, mobility, physical and cognitive function analysis can be used for early detection of mobility decline, early detection of physical or cognitive function decline in the user's habitual setting, using data collected from passive monitoring of daily activities or active monitoring of prescribed test routines. User feedback may also include actionable feedback on which aspect of the function is on decline and recommend an action to prevent or slow down the decline.

In some implementations, associated mobile app may have accounts for users or caregivers that can be used to view relevant user metrics or feedback. Associated mobile app can be used to enter relevant health information such as medications or health diagnosis or may be configured to get environmental conditions such as temperature to get context-aware information from the system. Associated mobile app can also be used to initiate prescribed tests that include clinically meaningful tests such as but not limited to 30 seconds sit-to-stand test, dual task walking and timed-up-and-go. The visual or audible feedback that the user can view using the mobile app may include historical trends for various performance scores such as strength score, mobility score and cognitive score derived from active monitoring of user performance on clinically meaningful tests or passive monitoring of daily activities. Feedback may include context aware details such as increased fall risk that may be caused by recently prescribed medication. Also, mobile app may be configured to call a selected caregiver when an impactful fall is detected.

In some implementations, Bluetooth beacons can be added to the system for fall detection, fall prediction, mobility, physical and cognitive function analysis in order to detect fall location or to quantify interaction time (i.e., social isolation). In some implementations, various components of the system for fall detection, fall prediction, mobility, physical and cognitive function analysis can communicate with each other directly using means such as but not limited to Bluetooth, Wi-Fi, LoRaWan, Zigbee, Cellular, etc.

The present solution combines a number of separate aspects that can be used together or separately to enable fall detection, fall prediction, mobility, physical and cognitive function analysis.

Disclosed features of the invention such as details of modules, combinations of components and other advantages will now be more specifically described with reference to the drawings. It will be understood that the specific method and system embodying the invention are shown by way of illustration and not a limitation of the invention. The principles and features of this invention may be employed in various and numerous embodiments without departing from the scope of the invention by the appended claims.

DETAILED DESCRIPTION

Detailed description is aimed to provide the means to any person skilled in the art to make and use the embodiments. In addition, the description is given in the context of a specific application and its necessities and changes made to the disclosed embodiments will be obvious to those skilled in the art. The general principles disclosed herein can be implemented to various other embodiments and operations while remaining in the essence and extent of the given disclosure which means the present disclosure is not limited to the shown embodiments and to be accorded the widest extent consistent with the principles and attributes disclosed herein.

As used herein, the term "and/or" includes any and all combinations of one or more of the associated listed items. Further, the singular forms and the articles "a", "an", and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Figure 1:
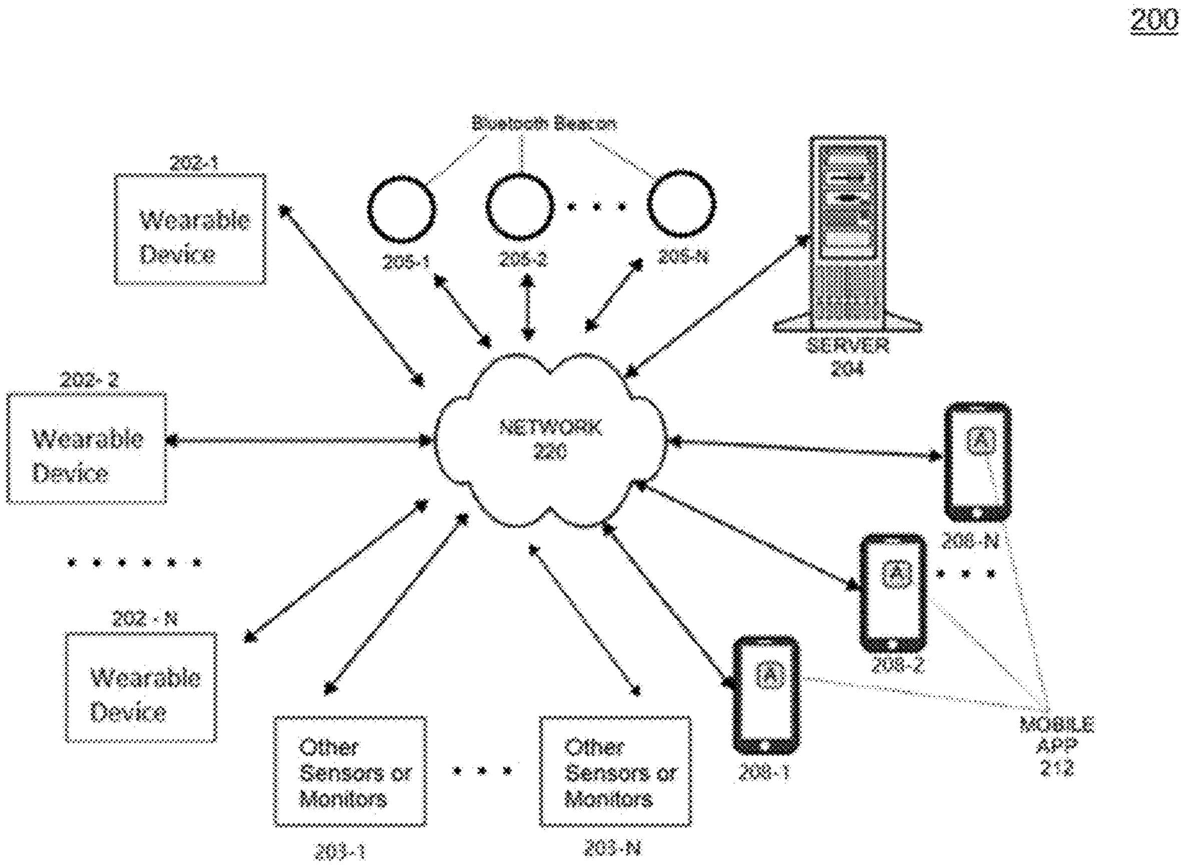
FIG. 1 shows a block diagram of the disclosed system for fall detection, fall prediction, mobility, physical and cognitive function analysis in line with some embodiments described herein.

Persons with mobility, cognitive deficits and/or other health conditions present a higher risk of falling and falls can lead to serious injuries. Hence it is important to both detect the falls and report to caregivers for immediate medical attention. It is also important to predict falls before they happen and detect contributing factors and intervene to reduce the likelihood of falls. Present disclosure is directed to a system intended for fall risk assessment, fall detection, fall prediction, active monitoring of user performance on clinically meaningful assessments such as but not limited to: sit-to-stand test or timed-up-and-go test, dual task assessment, passive monitoring and recording metrics related to user mobility, cognitive function, health, user functional health status, etc., that can be used by such persons in unsupervised settings or by clinicians in supervised settings, or for remote supervision. Passive monitoring refers to collecting user data without any additional user action such as monitoring of daily actions of the user whereas active monitoring refers to collecting data from a prescribed clinically relevant test routine which is activated by the user. Disclosed system for fall detection, fall prediction, mobility, physical and cognitive function analysis can include various software modules such gait analysis module, sit-to-stand analysis module, turn analysis module, balance test assessment module, fall prediction module, fall detection module and lastly; fall risk, mobility, physical function and cognitive function assessment module. Software modules can be used to process data or generate feedback. FIG. 1 depicts the system for fall detection, fall prediction, mobility, physical and cognitive function analysis in accordance with some embodiments described herein. In some implementations, disclosed system for fall detection, fall prediction, mobility, physical and cognitive function analysis may include: one or more wearable devices with previously disclosed features, a server, associated mobile app all of which are connected through a network. Some implementations may also include other sensors or monitors such as heart-rate sensors, blood pressure sensors, and other monitors etc., which may also be in the form of a wearable. Wearable device network interface may be configured to transfer data between wearable device, server and associated mobile app. Some embodiments may include one or more Bluetooth beacons. In some implementations, various components of system for fall detection, fall prediction, mobility, physical and cognitive function analysis can communicate with each other directly, such as but not limited to when a fall is detected and a wearable device can directly connect to Bluetooth beacons in order to get location information via Bluetooth beacons in order to provide it to caregivers or emergency help for location identification, or through providing this information through a Smart home integration.

Figure 2:
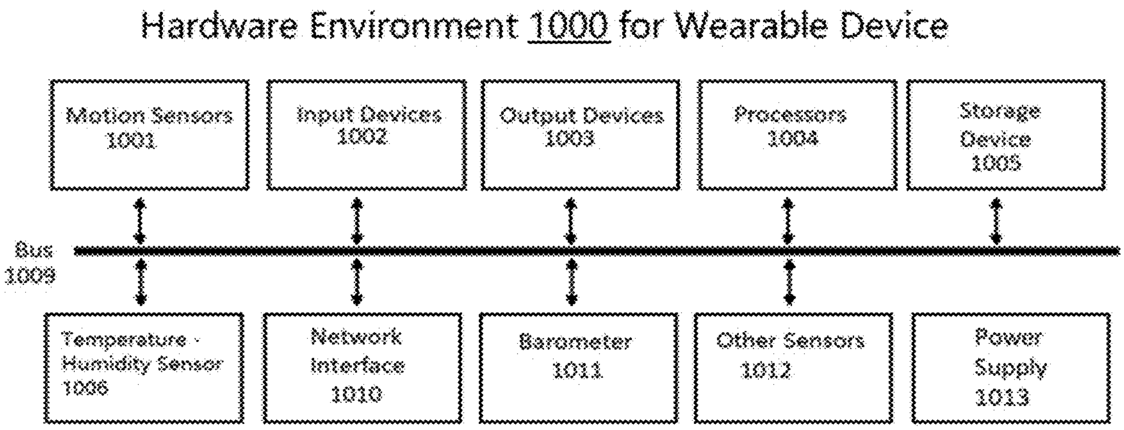
FIG. 2 is a block diagram depicting computing system of the wearable devices as shown in FIG. 1

Specifically, this system for fall detection, fall prediction, mobility, physical and cognitive function analysis includes one or more wearable devices. As shown in FIG. 2, a wearable device 1000 may have a power supply 1013, one or more motion sensors 1001 such as but not limited to accelerometers and gyroscopes for detecting motion of the device and providing data of the detected motions. Wearable device 1000 also may include one or more output device 1003 such as but not limited to speakers, used to provide notice, alarm or feedback to the user. Wearable device also may include one or more input devices 1002 such as but not limited to buttons or microphones. Microphones can be used to receive feedback from the user when a fall is detected using a wake word, and if the user fails to respond to audio feedback given using output devices 1003 after a fall, caregivers can be alerted. Wearable device 1000 also may include one or more processors 1004 for monitoring motion, for processing one or more metrics of the user, for determining when user falls using fall detection module. In some implementations, wearable device 1000 may further include a storage device 1005 to store sensor data. Processors 1004 may be further configured to store and retrieve motion data from memory. In some implementations, wearable device 1000 may be worn as a freely moving pendant or can be attached to the user's trunk with either straps or clips. In some implementations wearable device 1000 may include other sensors 1012 such as but not limited to barometer, temperature/humidity sensor. Wearable device may also include network interface 1010 such as Wi-Fi, Bluetooth, LoRaWan, Zigbee, Cellular, etc. FIG. 2 depicts the hardware environment of the wearable device 1000 in accordance with some embodiments described herein. Any device that includes disclosed sensors and features for instance accelerometers, gyroscope, audio input-output capability etc. such as Smart watches, or Smart phones, or other wearables can serve as a substitute to the disclosed wearable device using a specifically designed mobile app.

As can be seen in FIG. 1 system for fall detection, fall prediction, mobility, physical and cognitive function analysis 200 includes one or more wearable devices 202-1, 202-2, . . . , 202-N, one or more Bluetooth beacons 205-1, 205-2, . . . , 205-N, other sensors or monitors 203-1, 203-2, . . . , 203-N, server 204, mobile app 212 which is installed on one or more mobile devices 208-1, 208-2, . . . , 208-N that communicate through a network 220. However, other embodiments of the disclosed system for fall detection, fall prediction, mobility, physical and cognitive function analysis can include additional functional elements or omit one or more of the elements shown in FIG. 1 without departing from the scope of the present disclosure. Some of the software modules disclosed previously can work on wearable devices such as fall detection module and others such as gait analysis module can work on server 204 in order to increase battery life of the wearable devices. Server 204 can be used to store data; process data using previously disclosed software modules and generate user feedback.

In some implementations, the server 204 in the disclosed system for fall detection, fall prediction, mobility, physical and cognitive function analysis 200 may be configured to collect outputs of the one or more previously disclosed wearable devices, process the wearable device outputs that may include scores on user performance related to user mobility, cognitive function, base fall risk, machine learning based fall predictions, generate feedback on user performance and transmit them to associated mobile app.

Bluetooth beacons 205-1, 205-2, . . . , 205-N can be used for fall location identification and then can be used to provide crucial information to the first responders about the location of the resident within a site. The wearable devices detect beacons by their Generic Attribute Profile (GATT) service and therefore do not require any prior configuration to be "paired" with the beacons. The communication between the beacon and the wearable is intended to determine the closest beacon or triangulate an approximate location by using the "Received Signal Strength Indicator" (RSSI) information.

In some implementations the wearables can be designed to communicate with each other in a peer-to-peer type topology over Bluetooth Low Energy (BLE) in order to quantify time spent between each wearable. Each wearable device is both able to provide unique information about the wearer and obtain information from another wearable which is providing the same information for its wearer. This information is later processed to determine who is present for each interaction and the length of each interaction.

In some implementations, disclosed system for fall detection, fall prediction, mobility, physical and cognitive function analysis can include multiple other sensors or monitors 203-1, 203-2, . . . , 203-N such as a heart rate monitor to provide additional data on user functional health status. This data can be further analyzed in server 204 using a software module that uses methods such as fractal analysis to get additional information on user function as well as physiological function.

In some implementations, disclosed system for fall detection, fall prediction, mobility, physical and cognitive function analysis can be used for both active monitoring, where the user does a prescribed clinically relevant test routine which may include tests like normal walk, dual-task walk, fast walk, 30 second sit-to-stand-test, timed-up and go, balance test or for passive monitoring, where the disclosed system collects metrics as the subject performs normal activities of daily living in order to collect relevant user data for fall risk, mobility, physical or cognitive function assessment.

In some implementations, some of the user feedback generated by the disclosed system for fall detection, fall prediction, mobility, physical and cognitive function analysis may be generated by wearable devices 202-1, . . . , 202-N or server 204 can be specifically designed to be actionable so the user can use the feedback to reduce fall risk and prevent future falls and can be transmitted to associated mobile app 212 installed in mobile device 208-1, . . . , 208-N through network 220.

In some implementations, associated mobile app 212 may have accounts for users or caregivers that can be used to view relevant user metrics or feedback. Mobile app 212 can be used to enter relevant health information or may be configured to get environmental conditions such as temperature and humidity, to provide context-aware information. Mobile app 212 can also be used to initiate prescribed tests that include clinically meaningful tests such as but not limited to 30 seconds sit-to-stand test, dual task walking and timed-up-and-go. In one embodiment of the system for fall detection, fall prediction, mobility, physical and cognitive function analysis the prescribed test routine is as follows: 2-minute walk test, 1-minute dual task walking test, 30 seconds fast walk, timed-up-and-go, 30 seconds sit-to-stand. Users can be given instructions on how to complete the prescribed test routine using the output device wearable device. The prescribed test routine can be changed to include additional clinically relevant tests or exclude tests in other cases. The feedback that users can view using the mobile app 212 may include historical trends for various performance scores such as strength score, mobility score and cognitive score derived from active monitoring of user performance on clinically meaningful tests or passive monitoring of daily activities. Feedback may include context aware details such as early signs of cognitive decline. Also, mobile app 212 may be configured to call a selected caregiver when an impactful fall is detected. In some implementations, mobile app 212 can be configured to have different authorization levels for users and caregivers such that an authorized caregiver can view user functional health status or feedback of the users that wear wearable devices 202-1, . . . , 202-N.

In some implementations, disclosed system for fall detection, fall prediction, mobility, physical and cognitive function analysis can be used for early detection of mobility decline, early detection of physical or cognitive function decline in the user's habitual setting, using data collected from passive monitoring of daily activities or active monitoring of prescribed test routines. User feedback may also include actionable feedback generated on server 204 on which aspect of the function is on decline and recommend an action to prevent or slow down the decline and can be viewed by the users using mobile app 212 installed in mobile devices 208-1, . . . , 208-N.

Figure 3:
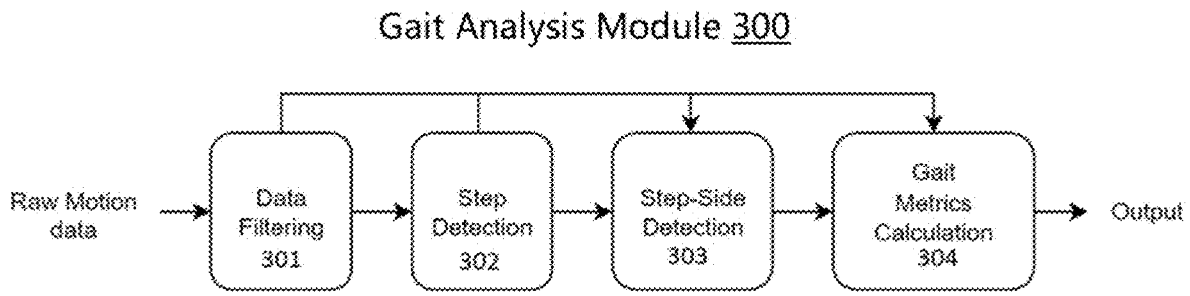
FIGS. 3-4-5-6-7-8-9 are flowcharts of modules used for assessing user mobility, physical and cognitive functions, predicting falls, detecting falls.

FIG. 3 shows a flowchart of gait analysis module 300 which is one of the software modules that can be used in the disclosed system for fall detection, fall prediction, mobility, physical and cognitive function analysis and works in the server 204 shown in FIG. 2. Raw motion data captured by the wearable device is the input of the gait analysis module 300. The raw data firstly is processed by data filtering 301 to reduce noise. In one embodiment of the gait analysis module 300, a low pass filter is applied. After the filtering, processed data goes to step detection 302. Step detection 302 is done by detecting heel-strikes and toe-offs. After detecting the heel-strikes and toe-offs, step-side detection 303 is performed using acceleration data, which means detecting which step is performed with which leg. Finally, after the steps and step-sides are detected, gait metrics calculation 304 is performed. Step time is calculated as time between two heel-strikes. Other metrics that can be used in gait analysis such as number of steps, stride time variability, stance times, swing times, double support times, total walking duration are calculated using heel-strikes and toe-offs. Lastly distance traveled is calculated using accelerometer data and further used to calculate gait speed. All the calculated gait metrics disclosed are the outputs of the gait analysis module 300.

Figure 4:
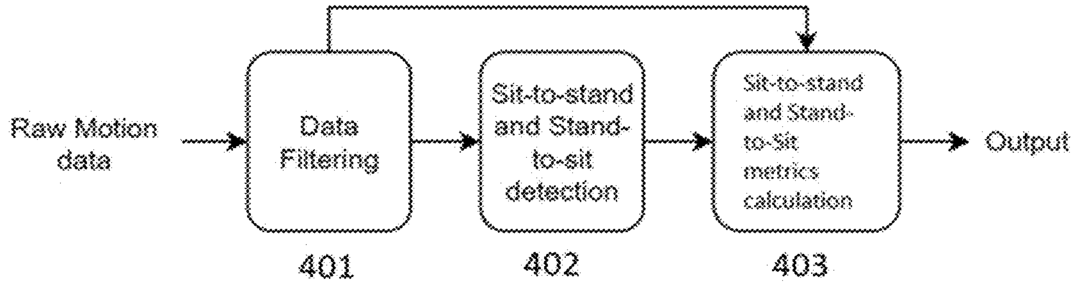

FIG. 4 shows a flowchart of sit-to-stand analysis module 400. Module is used to analyze both sit-to-stand movements and stand-to-sit movements. Raw motion data firstly goes through a data filtering 401. In one embodiment of the sit-to-stand analysis module 400, A low pass filter is applied to reduce noise. Filtered data is then passed to Sit-to-stand and Stand-to-sit detection 402. Sit-to-stand and stand-to-sit detection is done using vertical accelerations and rotational velocities around the left-right axis. Stand-to-sit movement is detected by using a threshold on both rotational velocity and vertical accelerations since the motion of standing up requires the torso to bend forward to balance the weight of the body on the feet and after the balancing motion the torso accelerates upwards. Stand-to-sit motion is detected similarly with a threshold on rotational acceleration around left-right axis and vertical acceleration as well since to sit down without falling once again requires the torso to accelerate towards ground while also torso bending forwards in order to balance the weight on the feet. After the movement is detected as a stand-to-sit or sit-to-stand transition, sit-to-stand and stand-to-sit metrics calculation 403 is initiated. Metrics such as total duration of the transition, minimum power during transition, maximum power during transition, average power during transition and initiation phase duration are calculated. Initiation phase is the preparation phase of a sit-to-stand transition which starts when a person starts the stand-to-sit transition and ends when the body does not have any contact with the chair.

Figure 5:
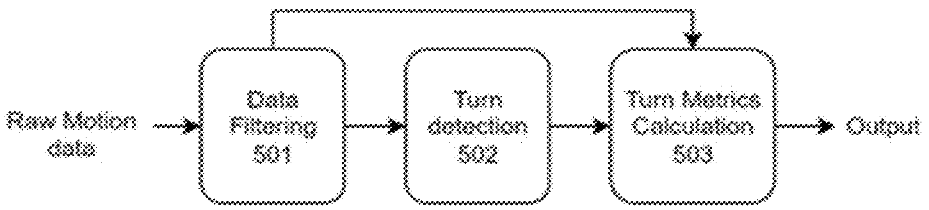

FIG. 5 shows a flowchart of turn analysis module 500. Module is used to analyze turns and can be installed into the server. Inputs of the turn analysis module 500 is raw motion data. Raw motion data firstly goes through data filtering 501 first, in one embodiment a low pass filter is applied to reduce noise. Filtered data is then passed onto turn detection 502. A turn is detected when the area under rotational velocity around the vertical axis curve exceeds a predetermined threshold which means the user has rotated more than a threshold. In one embodiment of the turn analysis module, if the user turns more than a set threshold, the movement is detected as a turn. After the turn is detected, turn metrics calculation 503 is initiated. Using the detected start and end times of the turn and rotational acceleration data, metrics such as average turn speed, maximum turn speed, turn duration, turn duration variability are calculated. All the calculated turn metrics disclosed are the outputs of the turn analysis module 500.

Figure 6:
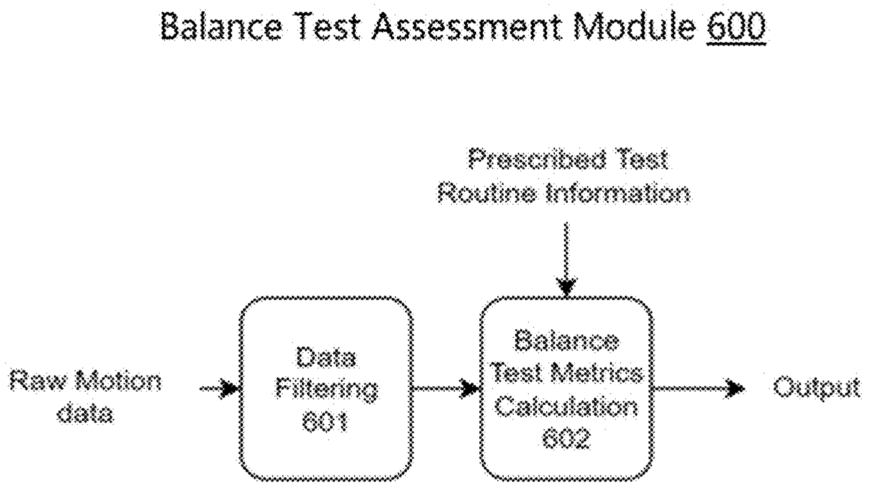

FIG. 6 shows balance assessment module 600, which is used to assess balance test using motion data. Firstly, raw data is processed to reduce noise using data filtering 601. In one embodiment of the balance assessment module 600, filtered data is passed to balance test metrics calculation 602. In balance test metrics calculation, motion data is used to calculate sway statistics such as sway path, maximum sway, average sway, % 95 confidence ellipse. Outputs of the balance assessment module are the metrics calculated in balance test metrics calculation 602.

Figure 7:
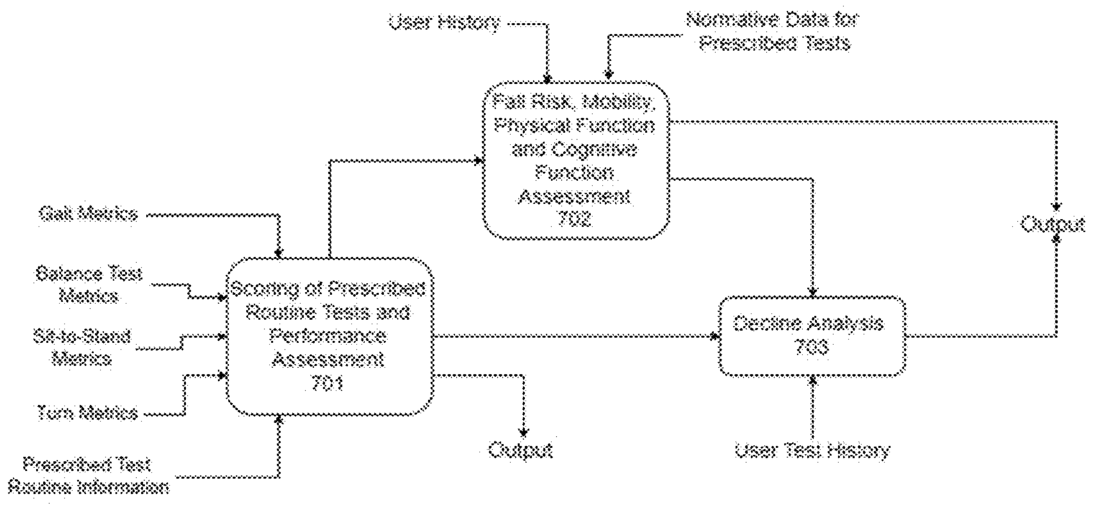

FIG. 7. shows fall risk, mobility, physical function and cognitive function analysis module 700. First step of this module is the scoring of routine tests and performance assessment 701. In this step, outputs from various other modules such as gait metrics, balance test metrics, sit-to-stand metrics, turn metrics and prescribed test routine information like start-end timings of tests on the test routine are gathered and processed to assess the user performance on routine prescribed tests, such as but not limited to 2-minute walk test, 30 seconds sit-to-stand test, balance test, timed-up-and-go test, dual walking test. Scoring of tests and performance varies by each test, in one embodiment of the module 30-second sit-to-stand test is primarily scored using number of sit-to-stands done in 30 second, timed-up-and-go test is scored using the time to complete the test, dual task walking test scored using dual task costs which is calculated using the difference of various gait metrics in normal walking versus walking while dual tasking. Test scores and user performance on the routine tests are sent to the server as an output to be stored and used later to detect if the user is on a decline or not. After the tests are scored, test scores and various metrics on the prescribed tests calculated by various modules are passed to Fall Risk, Mobility, Physical Function and Cognitive Function Assessment 702. Normative data for prescribed tests are an input of this step and used to compare the user performance to their expected performance considering their age, gender etc. In one embodiment, fall risk assessment is done by assessing various gait metrics such as gait speed and test scores on various tests such as 30 seconds sit-to-stand test, timed-up-and-go test etc. Also, user history is received as an input and user fall history is used in fall risk assessment since past falls are an indicator of fall risk. Mobility assessment is by scoring and assessing various metrics in timed-up-and-go test. In one embodiment, timed-up-and-go test score, turn metrics such as time to turn, gait metrics such as gait speed and sit-to-stand performance during timed-up-and-go test is used to assess mobility. Physical function assessment can be evaluated using various test scores and performances. In one embodiment, one aspect of the physical function assessed is lower extremity strength assessment is done by assessing user performance on 30 seconds sit-to-stand test scores and metrics such as sit-to-stand power. Another aspect of physical function assessed is gait speed reserve which is the difference of gait speed under normal walking and fast walking conditions done by evaluating gait speed in prescribed test routines of fast walking and normal walking. Another aspect of physical function assessment is frailty (i.e. physical reserve) which is defined as a clinically recognizable state of increased vulnerability resulting from aging-associated decline in reserve and function across multiple physiologic systems such that the ability to cope with stressors is compromised. The frailty assessment can be evaluated by gait speed in normal walk prescribed test and sit-to-stand metrics such as sit-to-stand power in 30 seconds sit-to-stand prescribed test. Cognitive function assessment can be evaluated by various gait metrics such as gait speed, dual task cost of various gait metrics such as stride time variability etc. Fall Risk, Mobility, Physical and cognitive function scores are the output of the fall risk, mobility, physical and cognitive function assessment 702. The scores are divided into three categories for user feedback purposes which are green for good—low risk, yellow for average—medium risk and red for poor—high risk. Lastly, data on fall risk, physical function and cognitive function assessment outputs and routine test scores and performances are passed to decline analysis 703. This step also receives the input "user test history" which is a record of user performance metrics and scores in previous tests in order to detect if there is a trend of decline on any of the functions or an increase in fall risk. If the user is detected to be on a decline, feedback about the user can be generated as an output to alert the user or caregivers on which function specifically is on decline using mobile app. Cognitive function decline can also be further analyzed to be used in early detection or detection of neurodegenerative diseases and dementias such as Alzheimer's Disease and Related Dementias (ADRD), Lewy Body Dementia (LBD), Parkinson's Disease, etc.

Figure 8:
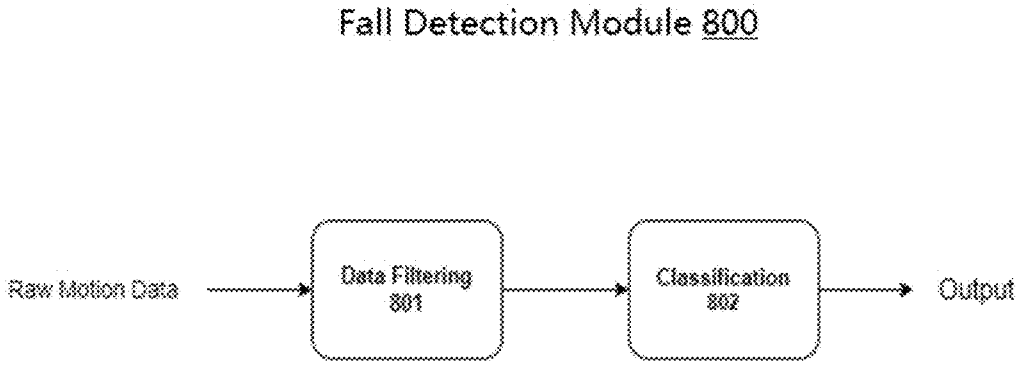

FIG. 8 shows the fall detection module 800. This module uses machine learning based classification algorithms to detect falls. Module works constantly in the wearable device in order to detect falls and provide notification in the event of a detected fall. In one embodiment, Input of the fall detection module 800 is motion data. Firstly, raw data is passed to data filtering 801. Afterwards, filtered data is sent to classification 802. In classification 802, filtered motion data such as accelerations are constantly monitored and analyzed using a machine learning based classification algorithm to check whether there is a fall or not. Classification algorithm used is a neural network. When a fall is detected, an output is sent to a server in order to achieve tasks such as alerting of the fall event, etc.

Figure 9:
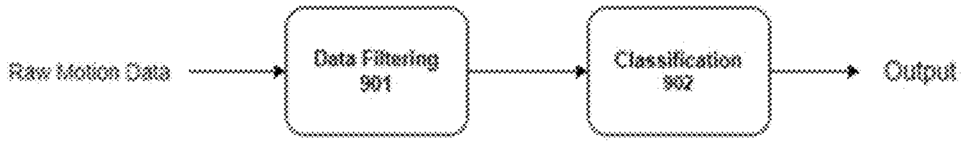

FIG. 9 shows the fall prediction module 900. This module uses machine learning based classification models to identify when the user is at a significantly higher fall risk compared to baseline. Input of this module is motion data. In one embodiment of the fall prediction module 900, the first step is data filtering 901. Afterwards filtered data is passed onto classification 902. In classification 902, filtered motion data are analyzed using a machine learning based classification algorithm to check whether the user is at a fall risk significantly higher than the baseline. Classification algorithm used in classification 902 is support vector machine (SVM). When the user is detected to be at a fall risk significantly higher than the baseline an output is sent to the server that can be used to alert of a pending fall event, etc.

What is claimed is:

1. An end-to-end system, comprising of a hardware and software platform, for fall risk analysis, fall detection, fall prediction, and fall prevention, physical function, cognitive function, and executive function, wherein the system has a wearable or non-wearable device, comprising:

one or more sensors for detecting motion from the wearable device or non-wearable device, wherein the wearable device can be fixed or freely moving;

one or more processors monitoring motion and processing metrics of a user;

measuring baseline data of physical function, cognitive function, executive function, gait metrics, audio, and health parameters;

a memory storing one or more sensor data and the baseline data;

one or more input devices for receiving instructions and feedback from the user;

one or more output devices providing instructions and feedback to the user;

an application stored on the wearable device or non-wearable device, or in the back-end, assessing the user's mobility, physical function, cognitive function, and executive function, wherein the application can be performed remotely without clinician oversight;

the application further comprises a user interface that includes information on health conditions, metabolic conditions, comorbidities and medications taken;

monitoring user's performance, and assessments of gait; wherein the gait measures normal walk, fast walk, dual task walk, sit-to-stand test (STS), timed-up-and-go (TUG), and rotation around hip tests, and identify root causes of a fall risk;

algorithms assessing mobility, physical function, cognitive function, and executive function using assessments of the gait; wherein the gait measures normal walk, fast walk, dual task walk, sit-to-stand test (STS), timed-up-and-go test (TUG), and rotation around hip tests, and other gait metrics, provide fall-risk and fall-risk root cause metrics;

a fall detection machine learning algorithm identifying a fall;

a fall prediction machine learning algorithm combining health parameters, cognitive function, executive function, physical function, fall risk metrics and gait metrics, dual task gait, declining gait speed, and other gait metrics over a period of time;

predicting a fall based on the combined sensor metrics, the fall detection algorithm, the fall prediction algorithm, the gait metrics, health parameter metrics, environmental metrics, and audio processing;

accessing cognitive and executive function based on audio recordings of the user's performance of dual task gait and daily variations in dual task gait, in addition to gait metrics and physical function;

a Fractal Scale Index based algorithm to identify gait patterns in ADRD (Alzheimer's Disease and Related Dementias) and cardiovascular health;

transmitting feedback to the user if the gait and balance metrics is higher than the user's baseline metrics; wherein the feedback can be visual or audible;

transmitting feedback to the user if the physical function of the user is lower than the user's baseline metrics; wherein the feedback can be visual or audible;

transmitting feedback to the user if the cognitive function of the user is lower than the user's baseline metrics; wherein the feedback can be visual or audible; and transmitting feedback to the user if the executive function of the user is lower than the user's baseline metrics; wherein the feedback can be visual or audible.

2. The system as claimed in claim 1, further comprising an analysis providing indication of high-risk, medium-risk and low-risk fall risk categories.

3. The system as claimed in claim 1, wherein the wearable or non-wearable device is wirelessly connected to a back-end server and automatically uploads data without user intervention or the need of an intermediary mobile device, wherein the back-end server can be located on premise or on the cloud.

4. The system as claimed in claim 1, wherein the wearable or non-wearable device combines gait assessment, fall prediction, and fall detection, in a single device, wherein the single device operates independently of an intermediary mobile device and includes the ability to record voice and sound, provide voice guidance and respond to wake words.

5. The system as claimed in claim 1, further comprising a custom algorithm residing on the wearable or non-wearable device manipulating user voice recorded from the microphone so that the voice is not recognizable or traceable to a person when automatically uploaded to the back-end server.

6. The system as claimed in claim 1, further comprises the ability to automatically call for emergency help, either through an automatic fall detection algorithm or through a wake word via the wearable or non-wearable device.

7. The system as claimed in claim 1, further comprising location information, through additional sensors and custom algorithms, wherein the location information includes both geographic location and specific room location within a dwelling.

8. The system as claimed in claim 1, further comprising a context-aware software platform that includes health information and environmental conditions along with gait providing context to falls and reasons for falls, or physical function, or cognitive function, or executive function.

9. The system as claimed in claim 1, wherein the Application further comprises historical data of mobility, physical function, cognitive function, and executive function.

10. The system as claimed claim 1, wherein the Application further compares individual performance to a population-based dataset to indicate how their individual performance compares.

11. The system as claimed in claim 1, the system further comprising of user data output that can be shared with a caregiver or healthcare provider, wherein the data is user selectable.

12. The system as claimed in claim 1, wherein the platform provides measures of fall risk and balance improvement assessment, neurodegenerative cognitive status assessment, and physical reserve assessment, to provide measures of a Quality-of-Life assessment.

* * * * *